United States Patent
Dancsi et al.

(10) Patent No.: US 8,110,691 B2
(45) Date of Patent: Feb. 7, 2012

(54) INDUSTRIAL PROCESS FOR THE SYNTHESIS OF 17α-ACETOXY-11β-[4-(N,N-DIMETHYL-AMINO)-PHENYL]-19-NORPREGNA-4,9-DIENE-3,20-DIONE AND NEW INTERMEDIATES OF THE PROCESS

(75) Inventors: Lajosné Dancsi, Budapest (HU); György Visky, Budapest (HU); Zoltán Tuba, Budapest (HU); János Csörgei, Budapest (HU); Csaba Molnár, Budapest (HU); Endréné Magyari, Albertirsa (HU)

(73) Assignee: Richter Gedeon Nyrt., Budapest (HU)

( * ) Notice: Subject to any disclaimer, the term of this patent is extended or adjusted under 35 U.S.C. 154(b) by 532 days.

(21) Appl. No.: 12/303,160

(22) PCT Filed: May 18, 2007

(86) PCT No.: PCT/HU2007/000045
§ 371 (c)(1),
(2), (4) Date: Dec. 2, 2008

(87) PCT Pub. No.: WO2007/144674
PCT Pub. Date: Dec. 21, 2007

(65) Prior Publication Data
US 2009/0187032 A1      Jul. 23, 2009

(30) Foreign Application Priority Data
Jun. 14, 2006 (HU) .................... 0600491

(51) Int. Cl.
*C07J 7/00* (2006.01)
(52) U.S. Cl. ........................ 552/598; 552/502
(58) Field of Classification Search .............. 552/502, 552/598
See application file for complete search history.

(56) References Cited

U.S. PATENT DOCUMENTS

| | | | |
|---|---|---|---|
| 4,041,055 A | 8/1977 | Shephard et al. | |
| 4,954,490 A | 9/1990 | Cook et al. | |
| 5,929,262 A * | 7/1999 | Kim et al. | 552/598 |
| 6,512,130 B1 * | 1/2003 | Hazra et al. | 552/648 |
| 6,768,014 B2 * | 7/2004 | Kim et al. | 552/595 |
| 7,449,572 B2 * | 11/2008 | Nique et al. | 540/113 |
| 7,868,194 B2 * | 1/2011 | Costantino et al. | 552/555 |

FOREIGN PATENT DOCUMENTS
WO      2004/078709 A2      9/2004

OTHER PUBLICATIONS

Gebhard et al., "11,21-Bisphenyl-19-norpregnane derivatives are selective antiglucocorticoids", Bioorg. Med. Chem. Lett, 1997, vol. 7, No. 17, pp. 2229-2234.
Livingston et al., "Intramolecular Cyanohydrin Elaboration. Construction of Corticosteroids from 17-Ketosteroids", J. Am. Chem. Soc., 1990, vol. 112, pp. 6449-6450.
Rao et al., "11beta-Substituted 12beta-ethyl gonane derivatives exhibit reversal of antiprogestational activity", Steroids, 1998, vol. 63, pp. 50-57.
Vanrheenen et al., "New Synthesis of Cortico Steroids from 17-Keto Steroids: Applications and Stereochemical Study of the Unsaturated Sulfoxide-Sulfenate Rearrangement", J. Org. Chem., 1979, pp. 1582-1584, vol. 44, No. 9.

* cited by examiner

Primary Examiner — Golam M M Shameem
(74) Attorney, Agent, or Firm — Jason D. Voight

(57) ABSTRACT

A new industrial process for the synthesis of solvate-free 17α-acetoxy-11β-[4-(N,N-dimethyl-amino)-phenyl]-19-norpregna-4,9-diene-3,20-dione [CDB-2914] of formula (I)

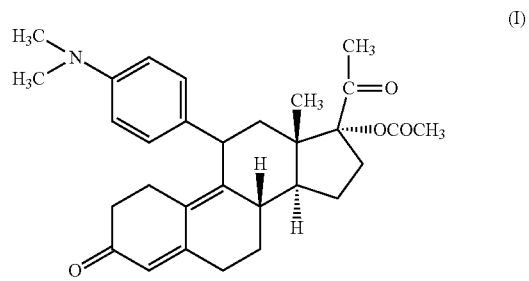

(I)

which is a strong antiprogestogene and antiglucocorticoid agent. The invention also relates to compounds of formula (VII)

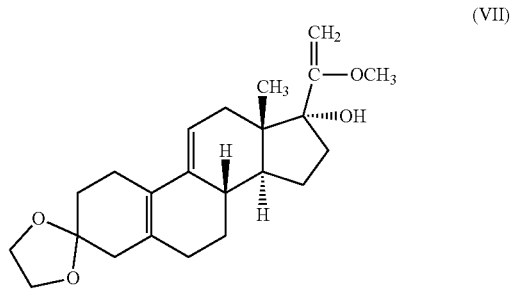

(VII)

and (VIII)

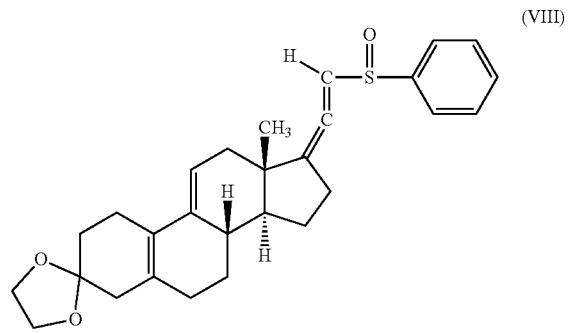

(VIII)

used as intermediates in the process.

5 Claims, 2 Drawing Sheets

(VII)

(VIII)

INDUSTRIAL PROCESS FOR THE SYNTHESIS OF 17α-ACETOXY-11β-[4-(N,N-DIMETHYL-AMINO)-PHENYL]-19-NORPREGNA-4,9-DIENE-3,20-DIONE AND NEW INTERMEDIATES OF THE PROCESS

This is the National Stage of International Application PCT/HU2007/000045, filed May 18, 2007.

The present invention relates to a new industrial process for the synthesis of solvate-free 17α-acetoxy-11β-[4-(N,N-dimethyl-amino)-phenyl]-19-norpregna-4,9-diene-3,20-dione [CDB-2914] of formula (I) which is a strong antiprogestogene and antiglucocorticoid agent. The invention also relates to compounds of formula (VII) and (VIII) used as intermediates in the process.

The names of the compounds of formulas of Roman numerals on the attached scheme are given in the description of the process according to the invention.

The process according to the invention is the following:

i) 3-(ethylene-dioxy)-estra-5(10),9(11)-diene-17-one of formula (X) is reacted with potassium acetilyde formed in situ in dry tetrahydrofuran by known method, ii) the obtained 3-(ethylene-dioxy)-17α-ethynyl-17β-hydroxy-estra-5(10),9(11)-diene of formula (IX) is reacted with phenylsulfenyl chloride in dichloromethane in the presence of triethylamine and acetic acid, iii) the obtained isomeric mixture of 3-(ethylene-dioxy)-21-(phenyl-sulfinyl)-19-norpregna-5(10),9(11),17(20),20-tetraene of formula (VIII) is reacted first with sodium methoxide in methanol, then with trimethyl phosphite, iv) the obtained 3-(ethylene-dioxy)-17α-hydroxy-20-methoxy-19-norpregna-5(10),9(11),20-triene of formula (VII) is reacted with hydrogen chloride in methanol, then v) the obtained 3-(ethylene-dioxy)-17α-hydroxy-19-nor-pregna-5(10),9(11)-diene-20-one of formula (VI) is reacted with ethylene glycol in dichloromethane in the presence of trimethyl orthoformate and p-toluenesulfonic acid by known method, vi) the obtained 3,3,20,20-bis(ethylene-dioxy)-17α-hydroxy-19-norpregna-5(10),9(11)-diene of formula (V) is reacted with hydrogen peroxide in a mixture of pyridine and dichloromethane in the presence of hexachloroacetone by known method, vii) the obtained 3,3,20,20-bis(ethylene-dioxy)-17α-hydroxy-5,10-epoxy-19-norpregn-9(11)-ene of formula (IV), containing approximately a 1:1 mixture of 5α,10α- and 5β,10β-epoxides, is isolated from the solution and reacted with a Grignard reagent obtained from 4-bromo-N,N-dimethyl-aniline in tetrahydrofuran in the presence of copper(I) chloride catalyst without separation of the isomers by known method, viii) the obtained 3,3,20,20-bis(ethylene-dioxy)-5α,17α-dihydroxy-11β-[4-(N,N-dimethylamino)-phenyl]-19-norpregn-9(11)-ene of formula (III) is reacted with potassium hydrogensulfate in water by known method, ix) the obtained 11β-[4-(N,N-dimethylamino)-phenyl]-17α-hydroxy-19-norpregn-4,9-diene-3,20-dione of formula (II) is acetylated with acetic anhydride in the presence of perchloric acid by known method, finally x) the solvate-free compound of formula (I) is liberated from the obtained solvate containing compound of formula (I) in a 1:1 mixture of ethanol and water at 70° C.

The synthesis of compound of formula (I) was first described in the U.S. patent U.S. Pat. No. 4,954,490 starting from 3-methoxy-19-norpregna-1,3,5(10),17(20)-tetraene. First the 17α,20α-diol is synthesized by oxidation of the 17(20)-double bond with osmium tetroxide, which is transformed into 3-methoxy-19-norpregna-2,5(10)-diene-17α,20α-diol by Birch reduction. Then the 4,9-diene structure is formed with pyridinium tribromide to furnish 17α,20α-dihydroxy-19-norpregna-4,9-diene-3-one, which is oxidized with oxalyl chloride to yield 17α-hydroxy-19-norpregna-4,9-diene-3,20-dione. Then the 3,3,20,20-bis(ethylene-dioxy)-19-nor-pregna-5(10),9(11)-diene-17α-ol is synthesized by ketal formation and the compound is reacted with metha-chlorperbenzoic acid to furnish 5α,10α-epoxy-3,3,20,20-bis(ethylene-dioxy)-19-norpregn-9(11)-ene-17α-ol. The latter is transformed into 3,3,20,20-bis(ethylene-dioxy)-5α,17α-dihydroxy-11β-[4-(N,N-dimethylamino)-phenyl]-19-norpregn-9(11)-ene by Grignard reaction with p-(N,N-dimethylamino)-phenyl-magnesium bromide in the presence of CuCl catalyst and finally the compound of formula (I) is obtained by acylation with a mixture of acetic anhydride and phosphoric acid. This is a 10-step synthesis, the total yield of which is 0.62%, consequently it is not suitable for industrial production of the active ingredient.

According to the U.S. patent U.S. Pat. No. 5,929,262 the pregnane side-chain is synthesized by the so-called SNAP method, which is described in the following publication: J. Am. Chem. Soc., 112, 6449-6450 (1990). The starting material of the synthesis is 3,3-(ethylene-dioxy)-norandrosta-5(10),9(11)-diene-17-one, which is first transformed into 17α-hydroxy,17β-cyanhydrine. The latter is reacted with chloro-(chlormethyl)-dimethylsilane in the presence of 4-(N,N-dimethylamino)-pyridine to yield 17β-cyano-17α-[(chlormethyl)-dimethylsilyl]-estra-5(10),9(11)-diene, which is transformed into 17α-hydroxy-19-norpregna-4,9-diene-3,20-dione by intramolecular addition in the presence of lithium di-tert-butyl-biphenyl followed by reaction of the obtained product with hydrochloric acid. 17α-Hydroxy-19-norpregna-4,9-diene-3,20-dione is transformed without further purification into 3,3,20,20-bis(ethylene-dioxy)-17α-hydroxy-19-norpregna-5(10),9(11)-diene by reacting with ethylene glycol and trimethyl orthoformate in the presence of catalytic amount of p-toluenesulfonic acid. The following reaction step is the oxidation of the 5(10)-double bond with 30% hydrogen peroxide in the presence of hexafluoroacetone and disodium phosphate to epoxide. Then 3,3,20,20-bis(ethylene-dioxy)-5α,17α-dihydroxy-11β-[4-(N,N-dimethylamino)-phenyl]-19-norpregn-9-ene is obtained by Grignard reaction with p-(N,N-dimethylamino)-phenyl-magnesium bromide in the presence of CuCl catalyst and compound of formula (I) is synthesized by acylation with trifluoroacetic anhydride and acetic acid in the presence of p-toluenesulfonic acid catalyst. In the first steps of the 9-step process the applied reagents are hazardous from the point of environmental protection (alkali cyanides and metal lithium are used for the synthesis of cyanhydrine) and the reaction temperature is −70° C., which is disadvantageous in an industrial production. The total yield of the synthesis is 13%.

The patent application WO 2004/078709 describes the following modification of the above process: from 17α-hydroxy-19-norpregna-4,9-diene obtained according to the method mentioned above first the 17α-acetoxy derivative is synthesized by reacting with a mixture of acetic acid and trifluoroacetic anhydride. The next step is the formation of ketal from the oxo group in position 3 with ethylene glycol and triethyl orthoformate in the presence of p-toluenesulfonic acid to furnish 3,3-(ethylene-dioxy)-17α-acetoxy-19-norpregna-5(10),9(11)-diene-20-one. This is transformed into 5α,10α-epoxide derivative with 30% hydrogen peroxide in the presence of hexafluoroacetone and disodium hydrogenphosphate and the 5α-hydroxy-17α-acetoxy-3,3-(ethylene-dioxy)-11β-[4-(N,N-dimethylamino)-phenyl]-19-norpregn-9(10)-ene-20-one is obtained by Grignard reaction using only 2 equivalent of the reagent in contrary to the above mentioned processes. The final product of formula (I) is obtained by hydrolysis with aqueous acetic acid.

The synthesis of the 13-ethyl analogue of compound of formula (I) is described in the following publication: Steroids 63, 50-57 (1998). The starting material of the synthesis is levonorgestrel (17α-ethynyl-17β-hydroxy-13-ethyl-gon-4-en-3-one) and the reaction sequence is the following: first the 3,3-(ethylene-dioxy)-ketal is formed, from which the 17α-ethynyl-17β-hydroxy-13-ethyl-gona-4,9-diene-3-one is synthesized with piridinium tribromid via the $\Delta^{5(10)}$-derivative. Then the 17β-nitroxy derivative is synthesized followed by reacting it with a mixture of formic acid and dimethylformamide in the presence of mercury acetate to furnish 17α-formyloxy-13-ethyl-18,19-dinorpregna-4,9-diene-3,20-dione, which is hydrolyzed with potassium hydrogencarbonate to yield 17α-hydroxy-13-ethyl-18,19-dinorpregna-4,9-diene-3,20-dione and the latter is transformed into 3,3,20,20-bis(ethylene-dioxy) derivative. The further reaction steps in the synthesis of compound of formula (I) are the same as above (epoxide formation, Grignard reaction, hydrolysis of the ketal and acylation). The yield of the synthesis of 17β-nitroxy derivative and the formation of the side-chain is 29%, the total yield of the synthesis is 3.5%. Further disadvantage of the process is that the intermediates of the synthesis are purified by column chromatography, which is very expensive on industrial scale.

In the following publication: Bioorg. Med. Chem. Lett., 1997, 2229-2234, the synthesis of the 17α-ethynyl derivative and from this the 5α,10α-epoxide is described starting from 3,3-(ethylene-dioxy)-19-norandrosta-5(10),9(11)-diene-17-one—which is used as starting material in the process of our invention as well.

A process for the synthesis of pregnane side-chain—in the series of corticoids—is described in the U.S. patent U.S. Pat. No. 4,041,055 according to which the 21-(phenylsulfinyl)-pregnane derivative is obtained from the 17α-ethynyl-androstane derivative with phenylsulfenyl chloride in the presence of triethylamine, followed by Michael addition to furnish 20-methoxy-21-(phenylsulfinyl) derivative. The latter is reacted with trimethyl phosphite to yield the 17α-hydroxy-20-keto-pregnane derivative and the 17α-hydroxy-20-keto-pregnane is obtained by acid hydrolysis.

It is known that 3-(ethylene-dioxy)-17α-ethynyl-17β-hydroxy-estra-5(10),9(11)-diene of formula (IX) can be synthesized from 3-(ethylene-dioxy)-estra-5(10),9(11)-diene-17-one of formula (X), which is an industrial product readily available in large quantities. The basis of our invention is the discovery that the new 3-(ethylene-dioxy)-21-(phenylsulfinyl)-19-norpregna-5(10),9(11),17(20),20-tetraene of formula (VIII) can be synthesized starting from 3-(ethylene-dioxy)-17α-ethynyl-17β-hydroxy-estra-5(10),9(11)-diene of formula (IX) with phenylsulfenyl chloride in the presence of triethylamine and acetic acid in good yield and at higher temperature, than as it was described in the U.S. patent U.S. Pat. No. 4,041,055 (−70° C.). The new 3-(ethylene-dioxy)-17α-hydroxy-20-methoxy-19-norpregna-5(10),9(11),20-triene of formula (VII) can be obtained from compound of formula (VIII) by addition of methanol followed by reaction with trimethyl phosphite. The new 3-(ethylene-dioxy)-17α-hydroxy-19-norpregna-5(10),9(11)-diene-20-one of formula (VI) is synthesized from the 20-methoxy derivative by hydrolysis with hydrochloric acid. The known 3,3,20,20-bis(ethylene-dioxy)-17α-hydroxy-19-norpregna-5(10),9(11)-diene of formula (V) is obtained from compound of formula (VI) in a ketal formation reaction with ethylene glycol in the presence of trimethyl orthoformate and p-toluenesulfonic acid. The desired product of formula (I) is synthesized from compound of formula (V) in 4 steps, but isolation of only 2 intermediates is necessary. First the 5α,10α-epoxide of formula (IV) is synthesized, then this is transformed into 5α-hydroxy-11-[4-(N,N-dimethylamino)-phenyl] derivative of formula (III) by Grignard reaction in the presence of CuCl catalyst. After acid hydrolysis the 17α-hydroxy-11β-[4-(N,N-dimethyl-amino)-phenyl]-pregna-4,9-diene-3,20-dione of formula (II) is obtained and the latter is acylated with a mixture of acetic anhydride perchloric acid to yield the desired compound of formula (I), which is transformed into solvate-free form.

The process according to our invention can preferably be carried out by reacting the 3-(ethylene-dioxy)-estra-5(10),9(11)-diene-17-one of formula (X) with potassium acetilyde—formed in situ from potassium tert-butoxide and acetylene—in dry tetrahydrofuran at a temperature between −5 and +5° C., preferably between 0 and −2° C. The obtained 3-(ethylene-dioxy)-17α-ethynyl-17β-hydroxy-estra-5(10),9(11)-diene of formula (IX) is reacted in a dichloromethane solution with a solution of 1.3 equivalent of phenylsulfenyl chloride in chloroform at a temperature between −10 and +5° C., preferably between 0 and −5° C., in the presence of 1.3 equivalent of triethylamine and 1.2 equivalent of acetic acid. The obtained 3-(ethylene-dioxy)-21-(phenyl-sulfinyl)-19-norpregna-5(10),9(11),17(20),20-tetraene of formula (VIII) is reacted first with 0.5 equivalent of sodium methoxide in methanol, then with 1.1 equivalent of trimethyl phosphate at a temperature between 50 and 60° C., preferably between 62 and 64° C. The obtained 3-(ethylene-dioxy)-17α-hydroxy-20-methoxy-19-norpregna-5(10),9(11),20-triene of formula (VII) is hydrolyzed with 0.08 equivalent of hydrogen chloride in methanol at a temperature between 20 and 25° C. The obtained 3-(ethylene-dioxy)-17α-hydroxy-19-norpregna-5(10),9(11)-diene-20-one of formula (VI) is reacted with 10 equivalent of ethylene glycol and 6 equivalent of trimethyl orthoformate in dichloromethane in the presence and p-toluenesulfonic acid at a temperature between 20 and 25° C. The obtained 3,3,20,20-bis(ethylene-dioxy)-17α-hydroxy-19-norpregna-5(10),9(11)-diene of formula (V) is reacted with 5 equivalent of 50% hydrogen peroxide solution in a mixture of pyridine and dichloromethane in the presence of 0.25 equivalent of hexachloroacetone at a temperature between −10 and +10° C., preferably between 0 and −2° C. The obtained 3,3,20,20-bis(ethylene-dioxy)-17α-hydroxy-5,10-epoxy-19-norpregn-9(11)-ene of formula (IV), containing a 55:45 mixture of 5α,10α- and 5β,10β-epoxides, is reacted in the next step without purification and separation of the isomers. The mixture of epoxides of formula (IV) is reacted with 5 equivalent of 4-(N,N-dimethylamino)-phenyl magnesium bromide—obtained from 4-bromo-N,N-dimethyl-aniline and magnesium—in tetrahydrofuran in the presence of CuCl catalyst at a temperature between 15 and 20° C. The obtained 3,3,20,20-bis(ethylene-dioxy)-5α,17α-dihydroxy-11β-[4-(N,N-dimethylamino)-phenyl]-19-norpregn-9(11)-ene of formula (III) is reacted with 2.5 equivalent of potassium hydrogensulfate in water at a temperature between 0 and 5° C., then the reaction mixture is extracted with dichloromethane. The obtained solution of 11β-[4-(N,N-dimethylamino)-phenyl]-17α-hydroxy-19-norpregn-4,9-diene-3,20-dione of formula (II) in dichloromethane is directly used in the final step of the synthesis, in the acylation of 17-hydroxy group. The solution of compound of formula (II) is reacted with 10 equivalent of acetic anhydride in the presence of 1.5 equivalent of 70% perchloric acid at a temperature between −10 and −40° C., preferably between −25 and −30° C. for 1 h. The obtained crude 17α-acetoxy-11β-[4-(N,N-dimethylamino)-phenyl]-19-norpregna-4,9-diene-3,20-dione of formula (I) is recrystallized from isopropanol, then solvate-free compound is liberated from the obtained solvate containing compound of formula (I) in a 1:1 mixture of ethanol and water.

The advantages of our invention are the following:

1) It can be carried out on industrial scale using commercially available starting material.

2) It is a 9-step process, but only the isolation of 7 intermediates is necessary.

3) A new process is applied in the series of norsteroids using phenylsulfenyl chloride in the synthesis of the side-chain. From the point of industrial applicability the advantage of this is that the reaction is carried out via the new intermediates of formulas (VIII) and (VII) at a temperature between 0 and −5° C., instead of −70° C. used in the synthesis of analogous compounds according to the literature.

4) It is not necessary to separate the isomeric mixture of 5α,10α- and 5β,10β-epoxides of compound of formula (IV) as the by-products formed during the synthesis can easily be separated in the next step.

5) The solvate-free product is obtained in a less dangerous solvent, a 1:1 mixture of ethanol and water at 70° C., than the flammable, explosive, industrially not applicable diethyl ether—the use of which is described in the literature.

Figures 1, 2, 3, 4, 5:
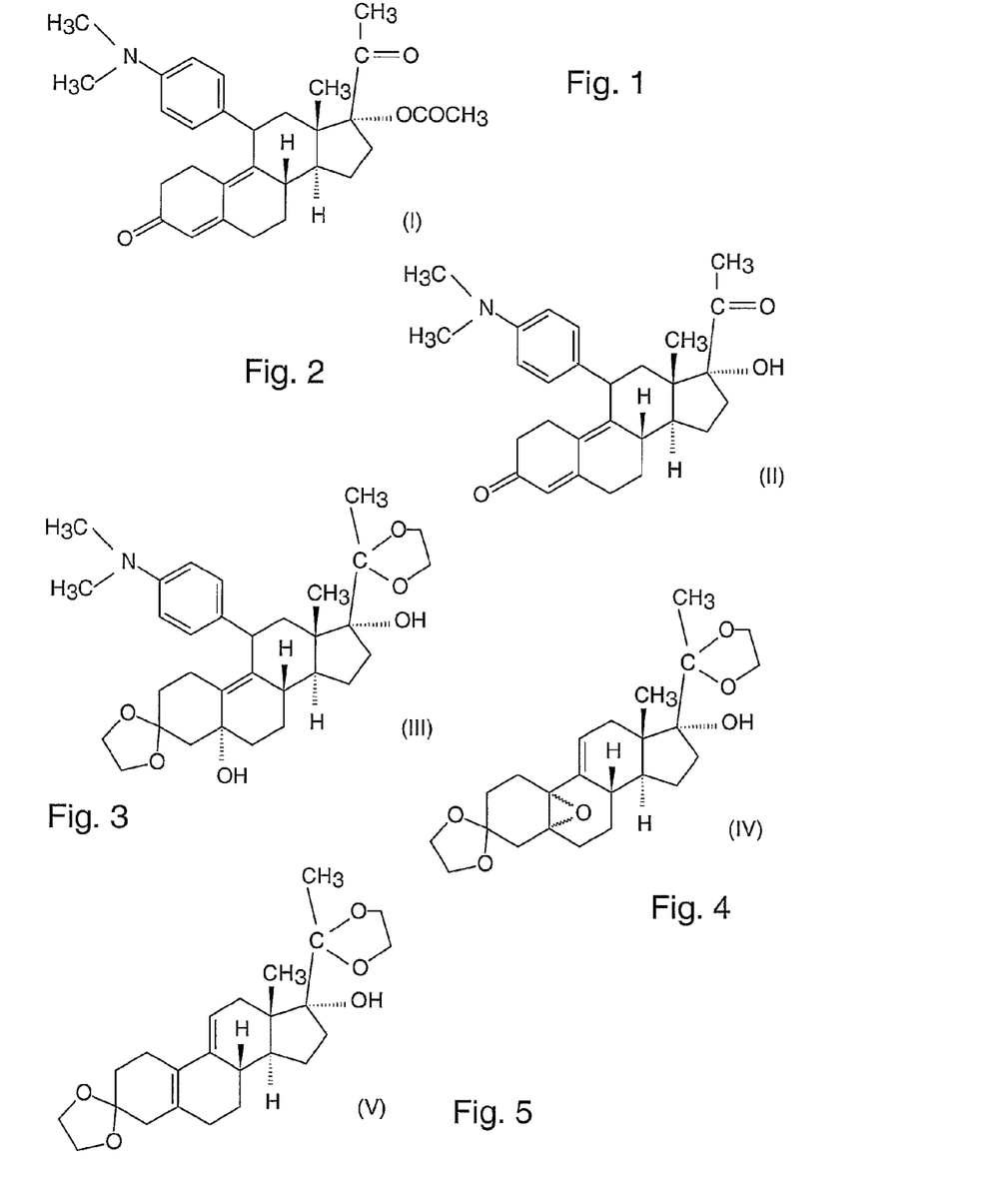
FIG. 1 shows formula (I).
FIG. 2 shows formula (II).
FIG. 3 shows formula (III).
FIG. 4 shows formula (IV).
FIG. 5 shows formula (V).
Figures 6, 7:
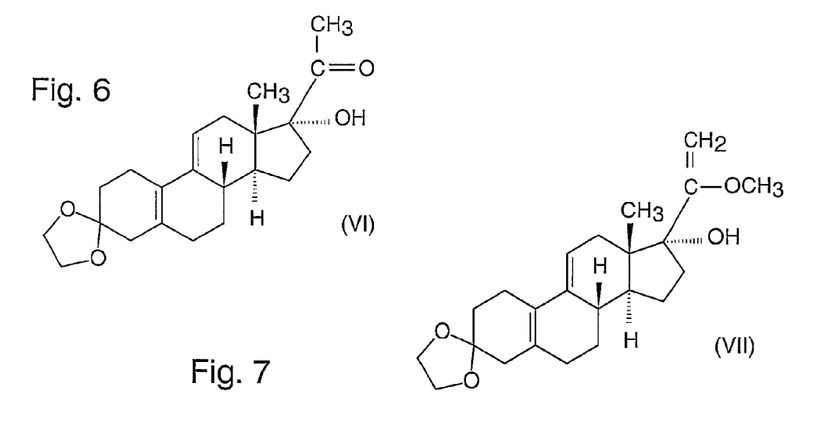
FIG. 6 shows formula (VI).
FIG. 7 shows formula (VII).
Figure 8:
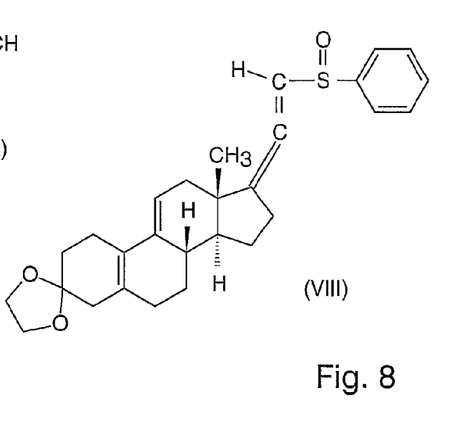
FIG. 8 shows formula (VIII).
Figure 9:
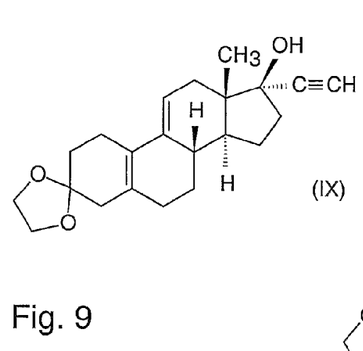
FIG. 9 shows formula (IX).
Figure 10:
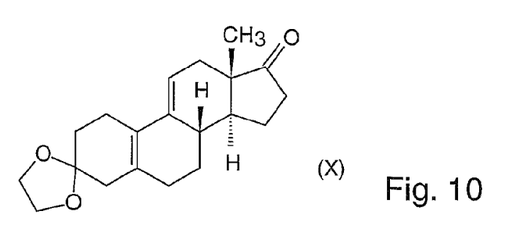
FIG. 10 shows formula (X).

The process according to our invention is illustrated by the following not limiting examples.

EXAMPLE 1

3-(Ethylene-dioxy)-17α-ethynyl-17β-hydroxy-estra-5(10),9(11)-diene (IX)

Under nitrogen potassium tert-butoxide (60 g) was dissolved in dry tetrahydrofuran (1500 mL) and acetylene was bubbled to the solution at 20° C. for 30 min, then the solution was cooled to 0-(−2) ° C. and bubbling of the acetylene was continued for a further 30 min. Then compound of formula (X) (119.4 g, 0.38 mol) was added while bubbling of the acetylene was continued. The reaction mixture was stirred for 1 h and nitrogen was bubbled through the mixture in order to remove the excess of acetylene. Saturated ammonium chloride solution (750 mL) was added and the reaction mixture was stirred for 10 min. The organic layer was separated and the water phase was extracted with tetrahydrofuran (300 mL). The combined organic layers were washed with saturated ammonium chloride solution (150 mL), concentrated to a volume of 600 mL and poured into ice-water (4 L). The obtained mixture was stirred for 30 min, the precipitated crystalline product was filtered off and dried at 40° C. to yield 122.8 g (95%) of the title compound. The purity of the product was min. 95% (according to HPLC).

EXAMPLE 2

3-(Ethylene-dioxy)-21-(phenyl-sulfinyl)-19-norpregna-5(10),9(11),17(20),20-tetraene (VIII)

To a suspension of compound of formula (IX) (122.5 g, 0.36 mol), triethylamine (151 mL) and acetic acid (24.6 mL) in dichloromethane (2200 mL) a solution of phenylsulfenyl chloride (67.9 g, 0.47 mol) in chloroform (170 mL) was added dropwise while keeping the temperature between 0 and −5° C. The reaction mixture was stirred for 10 min, then water (250 mL) and methanol (100 mL) was added. The organic layer was separated, washed with 1N hydrochloric acid and water, dried over sodium sulfate and concentrated to a volume of 185 mL. Diisopropyl ether (120 mL) was added to the residue and mixture was cooled to 5° C. The precipitated crystals were filtered off and dried below 60° C. to yield 144 g (88%) of the title compound. The purity of the product was min. 95% (according to HPLC).

Melting point: 176-180° C.

EXAMPLE 3

3-(Ethylene-dioxy)-17α-hydroxy-20-methoxy-19-norpregna-5(10),9(11),20-triene (VII)

To a solution of sodium methoxide (8.67 g, 0.16 mol) in methanol (4320 mL) compound of formula (VIII) (144 g, 0.321 mol) was added. The reaction mixture was stirred at 62-64° C. for 3 h, then trimethyl phosphite (42 mL, 0.35 mol) was added and stirring was continued at 62-64° C. for 2 h. The reaction mixture was cooled to 20° C. and poured into a solution of sodium chloride (288 g) in water (14 L). The precipitated crystalline product was filtered off, washed with water and dried at 40° C. to yield 80.2 g (67%) of the title compound. The purity of the product was min. 95% (according to HPLC).

Melting point: 128-132° C.

EXAMPLE 4

3-(Ethylene-dioxy)-17α-hydroxy-19-norpregna-5(10),9(11)-diene-20-one (VI)

A suspension of compound of formula (VII) (80 g, 0.27 mol) in a mixture of 1N hydrochloric acid (18 mL) and methanol (800 mL) was stirred at 20-25° C. for 40 min, then water of 10° C. (800 mL) was added and the reaction mixture was stirred for 30 min. The precipitated crystalline product was filtered off, washed with water and dried at 60° C. to yield 73 g (95%) of the title compound. The purity of the product was 98% (according to HPLC).

Melting point: 140-140° C.

EXAMPLE 5

3,3,20,20-Bis(ethylene-dioxy)-17α-hydroxy-19-norpregna-5(10),9(11)-diene (V)

To a solution of compound of formula (VI) (73 g, 0.2 mol) in dichloromethane (580 mL) ethylene glycol (126 mL, 2.26 mol), trimethyl orthoformate (132 mL, 1.21 mol) and p-toluenesulfonic acid (4.85 g) were added. The reaction mixture was stirred at 20-25° C. for 2 h, then saturated sodium hydrogencarbonate solution (380 mL) was added and stirring was continued for 30 min. The organic layer was separated, washed with water (400 mL), dried over sodium sulfate and concentrated to a volume of 175 mL. Methanol (230 mL) containing 0.5% pyridine was added and the solution was concentrated to a volume of 175 mL in order to remove dichloromethane. The obtained crystalline suspension was cooled to 0-2° C., stirred for 2 h, the precipitated product was filtered off and dried at 50° C. to yield 71.5 g (87%) of the title compound. The purity of the product was 98% (according to HPLC).

Melting point: 172-174° C.

EXAMPLE 6

3,3,20,20-Bis(ethylene-dioxy)-17α-hydroxy-5α, 10α-epoxy-19-norpregn-9(11)-ene (IV)

Under nitrogen to a solution of compound of formula (V) (71 g, 0.176 mol) in dichloromethane (360 mL) and pyridine (1.8 mL) hexachloroacetone (6.5 mL, 0.043 mol) and 50% hydrogen peroxide solution (51.5 mL, 0.9 mol) were added at 0-(-2)° C. and the reaction mixture was stirred at 0-2° C. for 3 h. Then dichloromethane (1800 mL) and ice-water (1440 mL) containing sodium thiosulfate (160 g) were added and the mixture was stirred at 0-10° C. for 30 min. The organic layer was separated, washed with water (300 mL), dried over sodium sulfate and concentrated under reduced pressure to yield 83 g of product, which is a 55:45 mixture of the 5α,10α- and 5β,10β-epoxides. The obtained crude mixture of epoxides was used in the next step without further purification.

EXAMPLE 7

3,3,20,20-Bis(ethylene-dioxy)-5α,17α-dihydroxy-11β-[4-(N,N-dimethylamino)-phenyl]-19-norpregn-9 (11)-ene (III)

A mixture of magnesium turnings (23.3 g, 0.97 mol) and 1,2-dibromoethane (0.35 mL) in tetrahydrofuran (44 mL) was stirred at 40-50° C. for 5 min, then the reaction mixture was cooled to 15° C. and a solution of 4-bromo-N,N-dimethylaniline (176 g, 0.88 mol) in tetrahydrofurane (1050 mL) was added at such a rate to keep the temperature below 15° C. Then the reaction mixture was stirred at 16-18° C. for 2 h to obtain the solution of the Grignard reagent.

The mixture of the epoxides (74 g, 0.176 mol)—obtained in the previous step—was dissolved in dichloromethane (300 mL) and copper(I) chloride (4 g) was added. The reaction mixture was stirred at 20-25° C. for 15 min, then cooled to 15° C. and the solution of the Grignard reagent was added over a period of 45 min. The reaction mixture was stirred at 20-25° C. for 2 h, then poured into water (1400 mL) containing ammonium chloride (170 g). The organic layer was separated, the water phase was extracted with dichloromethane (2×200 mL), the combined organic layers were washed with water (5×500 mL), dried over sodium sulfate and concentrated. The residue was dissolved in ethyl acetate (200 mL) at reflux temperature, the solution was cooled to −5° C. and the obtained crystalline suspension was kept at this temperature for 5 h. The precipitated product was filtered off and dried at 60° C. to yield 41.7 g (46%) of the title compound. The purity of the product was min. 95% (according to HPLC).

Melting point: 228-232° C.

EXAMPLE 8

11β-[4-(N,N-dimethylamino)-phenyl]-17α-hydroxy-19-norpregna-4,9-diene-3,20-dione (II)

To a solution of potassium hydrogensulfate (27.5 g, 0.2 mol) in water (230 mL) compound of formula (III) (41.7 g, 0.077 mol) was added at +5° C. and the reaction mixture was stirred at this temperature for 4 h. Then dichloromethane (230 mL) and a solution of potassium hydroxide (4.3 g) in water (40 mL) were added, the organic layer was separated and dried over sodium sulfate. Silicagel (7.5 g) was added and the dichloromethane solution was stirred at 20-25° C. for 30 min, then filtered. The filtrate was concentrated to a volume of 100 mL and the so obtained solution—containing 11β-[4-(N,N-dimethylamino)-phenyl]-17α-hydroxy-19-norpregna-4,9-diene-3,20-dione—was used in the next step.

EXAMPLE 9

17α-Acetoxy-11β-[4-(N,N-dimethylamino)-phenyl]-19-norpregna-4,9-diene-3,20-dione (I)

Acetic anhydride (73 mL, 0.77 mol) was cooled to −10° C. and 70% perchloric acid was added (10.8 mL, 0.124 mol). The so obtained solution was cooled to −30° C. and the solution of compound of formula (II)—obtained in the previous step—in dichloromethane (100 mL) was added at such rate to keep the temperature between −20 and −30° C., then the reaction mixture was stirred at this temperature for 1 h. The mixture was diluted with dichloromethane of 0° C. (300 mL) and poured into water (400 mL) containing sodium acetate (10.25 g, 0.125 mol). The organic layer was separated, washed with water (3×100 mL), dried over sodium sulfate and concentrated under reduced pressure. The obtained yellow syrupy material was crystallized from isopropanol (150 mL) to yield 27 g of the title compound in solvate form, containing 5-10% solvent. This material was dissolved in ethanol (230 mL) at 60° C., then warmed to 70° C. and ion-exchanged water (260 mL) was added. Nitrogen was bubbled through the so obtained solution, which was kept at 70° C. for 14 h. The solvate-free crystalline product gradually precipitated from the solution. The crystals were filtered at 70° C., washed with water of 70° C. and dried at 40° C. to yield 24 g (66%) of the title compound. The purity of the product was 99% (according to HPLC).

Melting point: 184-186° C.

EXAMPLE 10

3-(Ethylene-dioxy)-17α-ethynyl-17β-hydroxy-estra-5(10),9(11)-diene (IX)

Under nitrogen potassium tert-butoxide (22.6 kg) was dissolved in dry tetrahydrofuran (565 L) and acetylene was bubbled to the solution at 20° C. for 30 min, then the solution was cooled to 0-(−2)° C. and bubbling of the acetylene was continued for a further 30 min. Then compound of formula (X) (45 kg, 143 mol) was added while bubbling of the acetylene was continued. The reaction mixture was stirred for 1 h and nitrogen was bubbled through the mixture in order to remove the excess of acetylene. Saturated ammonium chloride solution (280 L) was added and the reaction mixture was stirred for 20 min. The organic layer was separated and the water phase was extracted with tetrahydrofuran (110 L). The combined organic layers were washed with saturated ammonium chloride solution (55 L), concentrated to a volume of 220 L and poured into ice-water (1500 L). The obtained mixture was stirred for 30 min, the precipitated crystalline product was filtered off and dried at 40° C. to yield 47.4 kg (97.2%) of the title compound. The purity of the product was min. 95% (according to HPLC).

EXAMPLE 11

3-(Ethylene-dioxy)-21-(phenyl-sulfinyl)-19-norpregna-5(10),9(11),17(20),20-tetraene (VIII)

To a suspension of compound of formula (IX) (40 kg, 117 mol), triethylamine (49 L) and acetic acid (8 L) in dichloromethane (720 L) a solution of phenylsulfenyl chloride (22.1 kg, 153 mol) in chloroform (55 L) was added dropwise while keeping the temperature between 0 and −5° C. The reaction mixture was stirred for 10 min, then water (80 L) and methanol (32 L) was added. The organic layer was separated, washed with 1N hydrochloric acid and water, dried over sodium sulfate and concentrated to a volume of 28 L. Diisopropyl ether (40 L) was added to the residue and mixture was cooled to 5° C. The precipitated crystals were filtered off and dried below 60° C. to yield 45.8 kg (87.3%) of the title compound. The purity of the product was min. 95% (according to HPLC).

Melting point: 176-180° C.

EXAMPLE 12

3-(Ethylene-dioxy)-17α-hydroxy-20-methoxy-19-norpregna-5(10),9(11),20-triene (VII)

To a solution of sodium methoxide (1.2 kg, 22.2 mol) in methanol (600 L) compound of formula (VIII) (20 kg, 44.6 mol) was added. The reaction mixture was stirred at 62-64° C. for 3 h, then trimethyl phosphite (5.8 L, 48.6 mol) was added and stirring was continued at 62-64° C. for 2 h. The reaction mixture was cooled to 20° C. and poured into a solution of sodium chloride (40 kg) in water (1940 L). The precipitated crystalline product was filtered off, washed with water and dried at 40° C. to yield 12.5 kg (75.3%) of the title compound. The purity of the product was min. 95% (according to HPLC).

Melting point: 128-132° C.

EXAMPLE 13

3-(Ethylene-dioxy)-17α-hydroxy-19-norpregna-5(10),9(11)-diene-20-one (VI)

A suspension of compound of formula (VII) (56 kg, 150 mol) in a mixture of 1N hydrochloric acid (12.6 L) and methanol (560 L) was stirred at 20-25° C. for 40 min, then water of 10° C. (560 L) was added and the reaction mixture was stirred for 30 min. The precipitated crystalline product was filtered off, washed with water and dried at 60° C. to yield 51.1 kg (95%) of the title compound. The purity of the product was 98% (according to HPLC).

Melting point: 140-140° C.

EXAMPLE 14

3,3,20,20-Bis(ethylene-dioxy)-17α-hydroxy-19-norpregna-5(10),9(11)-diene (V)

To a solution of compound of formula (VI) (49.3 kg, 137 mol) in dichloromethane (390 L) ethylene glycol (85 L, 1527 mol), trimethyl orthoformate (89 L, 818 mol) and p-toluenesulfonic acid (3.28 kg) were added. The reaction mixture was stirred at 20-25° C. for 2 h, then saturated sodium hydrogencarbonate solution (260 L) was added and stirring was continued for 30 min. The organic layer was separated, washed with water (270 L), dried over sodium sulfate and concentrated to a volume of 118 L. Methanol (150 L) containing 0.5% pyridine was added and then evaporated in order to remove dichloromethane. The obtained crystalline suspension was cooled to 0-(−2)° C., stirred for 2 h, the precipitated product was filtered off and dried at 50° C. to yield 48.33 kg (87%) of the title compound. The purity of the product was 98% (according to HPLC).

Melting point: 172-174° C.

EXAMPLE 15

3,3,20,20-Bis(ethylene-dioxy)-17α-hydroxy-5α,10α-epoxy-19-norpregn-9(11)-ene (IV)

Under nitrogen to a solution of compound of formula (V) (20 kg, 49.7 mol) in dichloromethane (100 L) and pyridine (0.5 L) hexachloroacetone (1.8 L, 12 mol) and 50% hydrogen peroxide solution (14.5 L, 253 mol) were added at 0-(−2)° C. and the reaction mixture was stirred at 0-2° C. for 3 h. Then dichloromethane (500 L) and ice-water (400 L) containing sodium thiosulfate (50 kg) were added and the mixture was stirred at 0-10° C. for 30 min. The organic layer was separated, washed with water (85 L), dried over sodium sulfate and concentrated under reduced pressure to yield 23.3 kg of product, which is a 55:45 mixture of the 5α,10α- and 5β,10β-epoxides. The obtained crude mixture of epoxides was used in the next step without further purification.

EXAMPLE 16

3,3,20,20-Bis(ethylene-dioxy)-5α,17α-dihydroxy-11β-[4-(N,N-dimethylamino)-phenyl]-19-norpregn-9(11)-ene (III)

A mixture of magnesium turnings (6.55 kg, 272 mol) and 1,2-dibromoethane (0.1 L) in tetrahydrofuran (13 L) was stirred at 40-50° C. for 5 min, then the reaction mixture was cooled to 15° C. and a solution of 4-bromo-N,N-dimethylaniline (49.5 kg, 247 mol) in tetrahydrofurane (300 L) was added at such a rate to keep the temperature below 15° C. Then the reaction mixture was stirred at 16-18° C. for 2 h to obtain the solution of the Grignard reagent.

The mixture of the epoxides (20.8 kg, 49.7 mol)—obtained in the previous step—was dissolved in dichloromethane (85 L) and copper(I) chloride (1.12 kg) was added. The reaction mixture was stirred at 20-25° C. for 15 min, then cooled to 15° C. and the solution of the Grignard reagent was added over a period of 45 min. The reaction mixture was stirred at 20-25° C. for 2 h, then poured into water (400 L) containing ammonium chloride (48 kg). The organic layer was separated, the water phase was extracted with dichloromethane (2×60 L), the combined organic layers were washed with water (5×140 L), dried over sodium sulfate and concentrated. The residue was dissolved in ethyl acetate (60 L) at reflux temperature, the solution was cooled to −5° C. and the obtained crystalline suspension was kept at this temperature for 5 h. The precipitated product was filtered off and dried at 60° C. to yield 12.6 kg (47%) of the title compound. The purity of the product was min. 95% (according to HPLC).

Melting point: 228-232° C.

EXAMPLE 17

11β-[4-(N,N-dimethylamino)-phenyl]-17α-hydroxy-19-norpregna-4,9-diene-3,20-dione (II)

To a solution of potassium hydrogensulfate (7.12 kg, 51.8 mol) in water (60 L) compound of formula (III) (11.7 kg, 21.7 mol) was added at +5° C. and the reaction mixture was stirred at this temperature for 4 h. Then dichloromethane (60 L) and a solution of potassium hydroxide (1.11 kg) in water (10 L) were added, the organic layer was separated and dried over sodium sulfate. Silicagel (2 kg) was added and the dichloromethane solution was stirred at 20-25° C. for 30 min, then filtered. The filtrate was concentrated to a volume of 26 L and the so obtained solution was used in the next step.

EXAMPLE 18

17α-Acetoxy-11β-[4-(N,N-dimethylamino)-phenyl]-19-norpregna-4,9-diene-3,20-dione (I)

Acetic anhydride (18.9 L, 199 mol) was cooled to −10° C. and 70% perchloric acid was added (2.8 L, 32.1 mol). The so obtained solution was cooled to −30° C. and the solution of compound of formula (II)—obtained in the previous step—in dichloromethane (26 L) was added at such rate to keep the temperature between −20 and −30° C., then the reaction mixture was stirred at this temperature for 1 h. The mixture was diluted with dichloromethane of 0° C. (80 L) and poured into water (100 L) containing sodium acetate (2.65 kg, 32.4 mol). The organic layer was separated, washed with water (3×25 L), dried over sodium sulfate and concentrated under reduced pressure. The obtained yellow syrupy material was crystallized from isopropanol (40 L) to yield 7 kg of the title compound in solvate form, containing 5-10% solvent. This material was dissolved in ethanol (60 L) at 60° C., then warmed to 70° C. and ion-exchanged water (67 L) was added. Nitrogen was bubbled through the so obtained solution, which was kept at 70° C. for 14 h. The solvate-free crystalline product gradually precipitated from the solution. The crystals were filtered at 70° C., washed with water of 70° C. and dried at 40° C. to yield 6.6 kg (64%) of the title compound. The purity of the product was 99% (according to HPLC).

Melting point: 184-186° C.

What we claim is:

1. Industrial process for the synthesis of solvate-free 17α-acetoxy-11β-[4-(N,N-dimethyl-amino)-phenyl]-19-norpregna-4,9-diene-3,20-dione of formula (I)

via ketal formation from 3-(ethylene-dioxy)-17α-hydroxy-19-norpregna-5(10),9(11)-diene-20-one of formula (VI)

epoxide formation in position 5,10 of the obtained 3,3,20,20-bis(ethylene-dioxy)-17α-hydroxy-19-norpregna-5(10),9 (11)-diene of formula (V)

reaction of the obtained 3,3,20,20-bis(ethylene-dioxy)-17α-hydroxy-5,10-epoxy-19-norpregna-9(11)-ene of formula (IV)

with the Grignard reagent obtained from bromo-N,N-dimethyl-aniline, deprotection of the so formed 3,3,20,20-bis (ethylene-dioxy)-5α,17α-dihydroxy-11β-[4-(N,N-dimethylamino)-phenyl]-19-norpregna-9(11)-ene of formula (III)

acetylation of the obtained 11β-[4-(N,N-dimethylamino)-phenyl]-17α-hydroxy-19-norpregna-4,9-diene-3,20-dione of formula (II)

and finally liberation of the solvate-free form of the desired product, characterized by i) reacting 3-(ethylene-dioxy)-estra-5(10),9(11)-diene-17-one of formula (X)

with potassium acetilyde formed in situ in dry tetrahydrofuran, ii) reacting the obtained 3-(ethylene-dioxy)-17α-ethynyl-17β-hydroxy-estra-5(10),9(11)-diene of formula (IX)

with phenylsulfenyl chloride in dichloromethane in the presence of triethylamine and acetic acid, iii) reacting the obtained isomeric mixture of 3-(ethylene-dioxy)-21-(phenyl-sulfinyl)-19-norpregna-5(10),9(11),17(20),20-tetraene of formula (VIII)

first with sodium methoxide in methanol, then with trimethyl phosphite, iv) reacting the obtained 3-(ethylene-dioxy)-17α-hydroxy-20-methoxy-19-norpregna-5(10),9(11),20-triene of formula (VII)

with hydrogen chloride in methanol, then v) reacting the obtained 3-(ethylene-dioxy)-17α-hydroxy-19-norpregna-5(10),9(11)-diene-20-one of formula (VI) with ethylene glycol in dichloromethane in the presence of trimethyl orthoformate and p-toluene-sulfonic acid, vi) reacting the obtained 3,3,20,20-bis(ethylene-dioxy)-17α-hydroxy-19-norpregna-5(10),9(11)-diene of formula (V) with hydrogen peroxide in a mixture of pyridine and dichloromethane in the presence of hexachloroacetone, vii) reacting the obtained 3,3,20,20-bis(ethylene-dioxy)-17α-hydroxy-5,10-epoxy-19-norpregn-9(11)-ene of formula (IV), containing approximately a 1:1 mixture of 5α,10α- and 5β,10β-epoxides, with a Grignard reagent obtained from 4-bromo-N,N-dimethyl-aniline in tetrahydrofuran in the presence of copper(I) chloride catalyst without separation of the isomers, viii) reacting the obtained 3,3,20,20-bis(ethylene-dioxy)-5α,17α-dihydroxy-11β-[4-(N,N-dimethylamino)-phenyl]-19-norpregn-9(11)-ene of formula (III) with potassium hydrogensulfate in water, ix) acetylation of the obtained 11β-[4-(N,N-dimethylamino)-phenyl]-17α-hydroxy-19-norpregn-4,9-diene-3,20-dione of formula (II) with acetic anhydride in the presence of perchloric acid, finally x) liberation of the solvate-free compound of formula (I) from the obtained solvate containing compound of formula (I) in a 1:1 mixture of ethanol and water at 70° C.

2. The process according to claim 1, characterized by using a chloroform solution of phenylsulfenyl chloride in step ii).

3. The process according to claim 1, characterized by carrying out the reaction with phenylsulfenyl chloride at 0-5° C. in step ii).

4. The process according to claim 1, characterized by carrying out the reaction with phenylsulfenyl chloride in the presence of 1.2 equivalent of acetic acid in step ii).

5. The process according to claim 1, characterized by carrying out the reaction with sodium methoxide and trimethyl phosphite at 62-64° C. in step iii).

* * * * *